United States Patent [19]

Wilkinson et al.

[11] 4,345,919
[45] Aug. 24, 1982

[54] DEGASSER FOR BIOLOGICAL FLUIDS

[75] Inventors: William R. Wilkinson, Mission City; Russell G. Sharp, Sugar Land; Charles C. Reed, Houston; Denton A. Cooley, Houston; Terry N. Crane, Houston, all of Tex.

[73] Assignee: Texas Medical Products, Inc., Houston, Tex.

[21] Appl. No.: 225,837

[22] Filed: Jan. 19, 1981

[51] Int. Cl.³ .............................................. B01D 19/00
[52] U.S. Cl. ......................................... 55/41; 55/204; 210/436; 210/456
[58] Field of Search ...................... 210/188, 512.1, 456, 210/436; 55/204, 205, 41; 422/48

[56] References Cited

U.S. PATENT DOCUMENTS

| | | | |
|---|---|---|---|
| 2,010,435 | 8/1935 | Matheson | 210/512 R X |
| 2,179,919 | 11/1939 | Carr et al. | 210/512.1 X |
| 2,762,451 | 9/1956 | McNeil | 55/204 |
| 3,753,336 | 8/1973 | Drew et al. | 210/512.1 X |
| 3,768,653 | 12/1981 | Brumfield | 210/436 X |
| 3,996,027 | 12/1976 | Schnell et al. | 55/41 X |
| 4,137,160 | 1/1979 | Eblihg et al. | 210/188 X |

Primary Examiner—Frank A. Spear, Jr.
Attorney, Agent, or Firm—H. Ross Workman; Allen R. Jensen; Drew S. Hamilton

[57] ABSTRACT

A device and method for its use in medical transfusion or bypass circuits wherein biological fluids, such as blood, are introduced onto the interior surface of an essentially cylindrical cavity in a vortical flow such that unwanted gas bubbles are separated from the biological fluids. The degassed biological fluids are collected and returned to the patient.

15 Claims, 5 Drawing Figures

DEGASSER FOR BIOLOGICAL FLUIDS

BACKGROUND

The present invention relates generally to a degassing device for biological fluids, sometimes referred to as a bubble trap. Bubble traps have been known and used for many years in the medical industry. Particularly, bubble traps are commonly used in the process of transmitting body fluids such as blood during various medical procedures such as transfusion.

During the process of a transfusion, it is possible to inadvertently introduce gaseous bubbles into the fluid as it passes through the circuit. If these bubbles are not removed, when the fluid is introduced into the blood stream, gaseous emboli may be created. Such emboli may become attached to, and occlude, the blood vessels. When this occurs, a common result is the development of dangerous infarcts. As additional material is collected by and adheres to the emboli, thrombosis may result.

Prior art bubble traps have attempted to avoid the transmission of gas bubbles into the blood stream by directing the transfused fluid along a wire-like surface designed to attract bubbles, and then into a settling basin wherein bubbles may rise out of the standing fluids. The degassed fluid is then transmitted from the bubble trap and may be infused into the blood stream.

A significant problem related to the process of removing gas bubbles through settling is the extended time period necessary to allow those bubbles to rise to the surface of the settling fluid. This problem is aggravated by the inability of smaller bubbles to rapidly rise to the surface due to their small density difference with respect to the surrounding fluid. Hence, it is difficult to ensure that all bubbles are removed with use of the bubble traps in direct body-to-body transfusion, or in cardiopulmonary bypass circuits. This is true since the flow of blood into the body must approximately equal the flow out of the body, and thus settling times are restricted and can be controlled only by varying the size of the settling container used in the bubble trap.

These problems are substantially circumvented through the use of the bubble trap of the present invention.

BRIEF SUMMARY AND OBJECTS OF THE INVENTION

The present invention comprises a novel apparatus and method for rapidly separating gas bubbles from biological fluids (such as blood) through the use of centrifugal forces acting upon both the gas bubbles and the biological fluids, venting the collected gases out of the first receptacle, and transferring the degassed fluid into a second receptacle wherein it is collected for transmission and infusion into the blood stream.

It is, therefore, a primary object of the present invention to provide for the effective removal of gas bubbles from biological fluids.

It is another object of the present invention to provide for rapid removal of gas bubbles from biological fluids in transfusion or bypass circuits.

These and other objects and features of the present invention will become more fully apparent from the following description and appended claims taken in conjunction with the accompanying drawings.

DETAILED DESCRIPTION OF THE PREFERRED EMBODIMENT

The Apparatus

Figure 1:
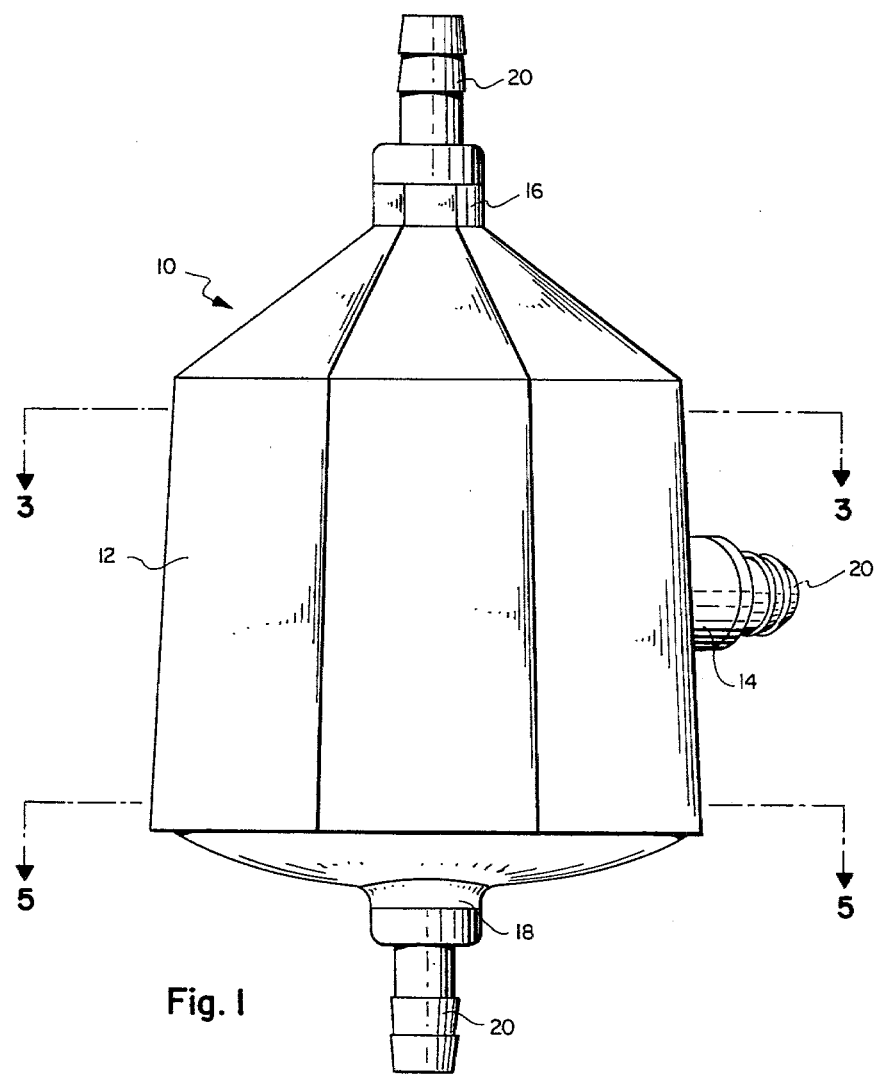
FIG. 1 is a front plan view of a presently preferred embodiment of the invention.

Reference is now made to the drawings wherein like parts are designated with like numerals throughout. Referring generally to FIG. 1, the bubble trap system, generally designated 10, is illustrated. The body 12 of the bubble trap 10 is a closed, portable rigid container formed of molded plastic. An inlet port 14 extends through the side wall of the container 12, providing a passage for introducing biological fluids into the bubble trap. A vent port 16 is positioned at the top of container 12 and extends through the upper portion of container 12 into the cavity thereof. Vent port 16 provides for the removal of gases extracted from the biological fluids. An exit port 18 is positioned at the bottom end of container 12 and extends through the lower portion of container 12 into the cavity thereof. Exit port 18 provides for removal of degassed biological fluids from container 12.

Ports 14, 16, and 18 provide for the attachment of connectors 20, which permit the interconnection of supply devices such as conventionally available medical tubing (not shown). It will be recognized that connectors 20 are well known in the art and are commonly available on the commercial market.

Figure 2:
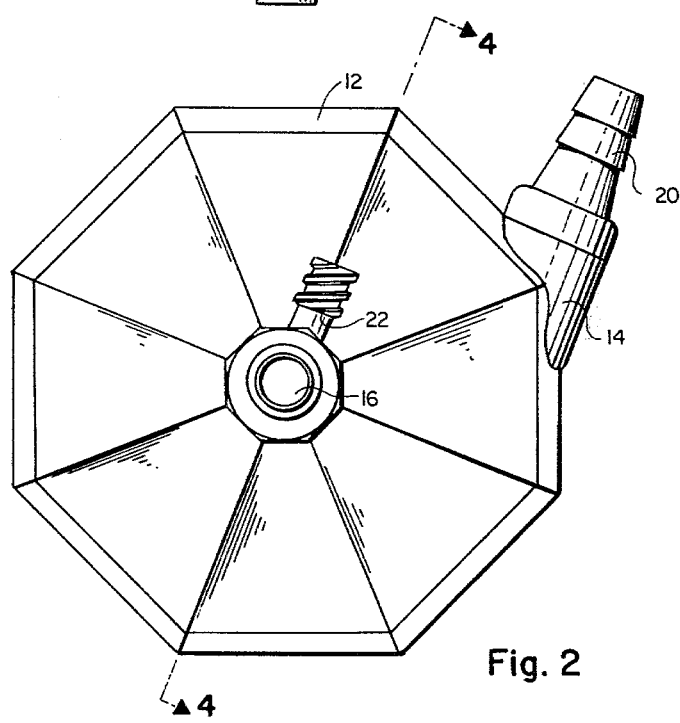
FIG. 2 is a top plan view of a presently preferred embodiment of the invention.

Referring to FIG. 2, a metering port 22 extends perpendicularly outward from the wall of the vent port 16. Meter port 22 additionally extends through the wall of vent port 16, thereby connecting to the interior passage of vent port 16. Meter port 22 preferably includes external threads providing for the attachment of a plug, conduit, pressure monitoring equipment, or similar devices.

Figure 3:
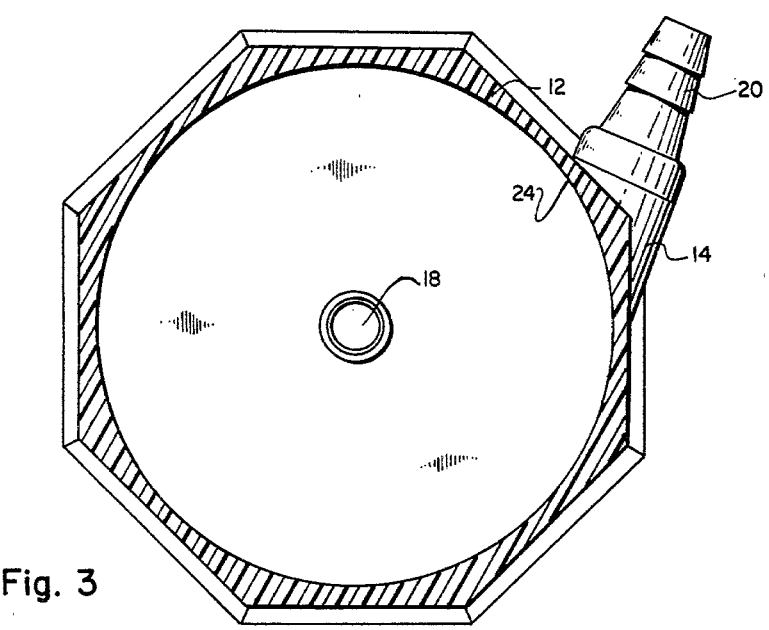
FIG. 3 is a top sectional view of a presently preferred embodiment of the invention wherein the separator plate is removed from the device, the view being taken along line 3—3 of FIG. 1.

By reference to FIG. 3 it is apparent that interior side wall 24 of container 12 is essentially round for creating a vortex action by the injection of fluid onto the surface of side wall 24. Injection port 14 is oriented so as to provide for the tangential injection of biological fluids from port 14 onto the side wall 24 of container 12. From FIG. 4, it becomes apparent that side wall 24 preferably slopes generally outwardly from top to bottom, thereby defining a truncated conical member. Side wall 24 has a shoulder 44 for purposes hereinafter more fully described. Side wall 24 intersects at its top with the lower edge of a concave ceiling surface 26. Vent port 16 extends upward from the apex of ceiling surface 26, through the top of container 12. A lip portion 28 extending outwardly from vent port 16 may be provided for receiving connector 20 such as by a press fit relationship, corresponding threads, or other suitable means of connection.

Floor member 32 is removably connected to container 12 by attachment of the outer ridges of said floor member 32 to container 12 at notch 34. Such attachment may be accomplished by a threadable connection between conforming surfaces, or by use of adhesive devices, or by other suitable means. The removability feature of floor member 32 permits access to the interior of container 12 for installation of a separating plate (or baffle) 36.

The interior surface of floor member 32 forms a concave floor surface 29. The bottom margin of container wall 24 intersects with the uppermost edge of concave floor surface 29. Floor surface 29 slopes downward and inward from its upper edge to a low point at its center, at which point exit port 18 extends outwardly through the floor member 32 to the atmosphere. A connecting lip 30 extends outwardly for receiving connector 20 in a press fit relationship, or by other suitable connecting means. The orifice of connector 20 aligns with the opening of port 18 to provide for transmission of fluids flowing from port 18 out of connector 20.

Separating plate 36, which is located in the lower portion of the interior of container 12, extends between the interior surfaces of side wall 24 so as to present a partition between a first chamber 38 and a second chamber 40 within the interior of bubble trap device 10.

Figure 4:
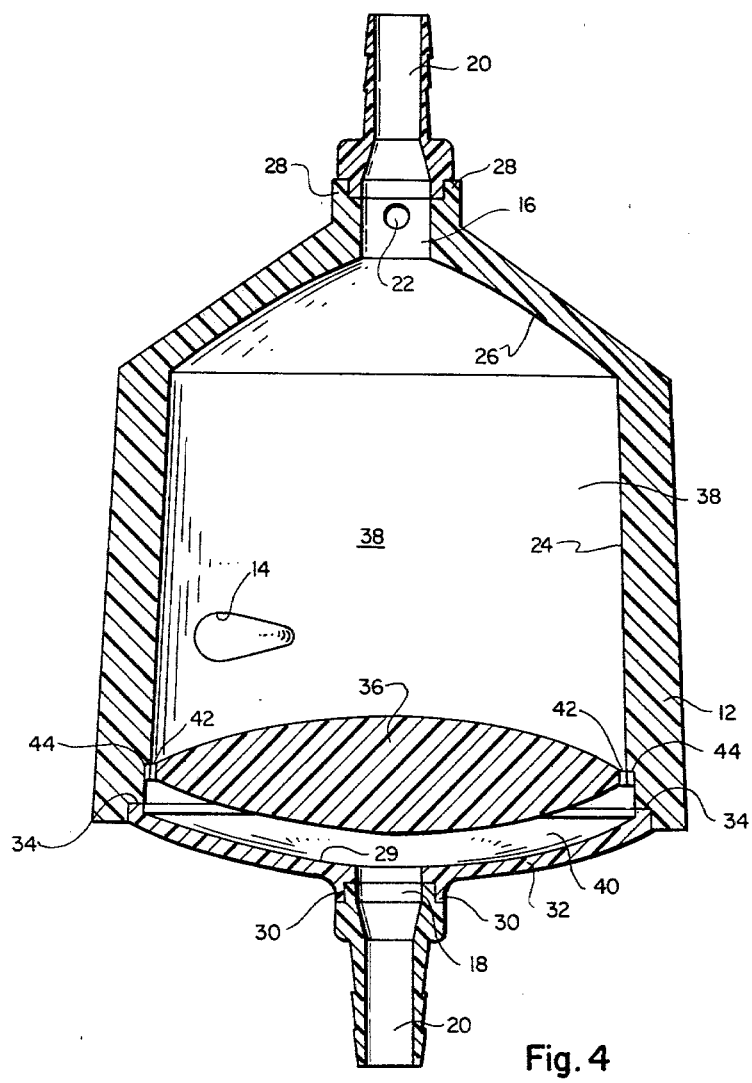
FIG. 4 is a front sectional view of a presently preferred embodiment of the invention along line 4—4 of FIG. 2.
Figure 5:
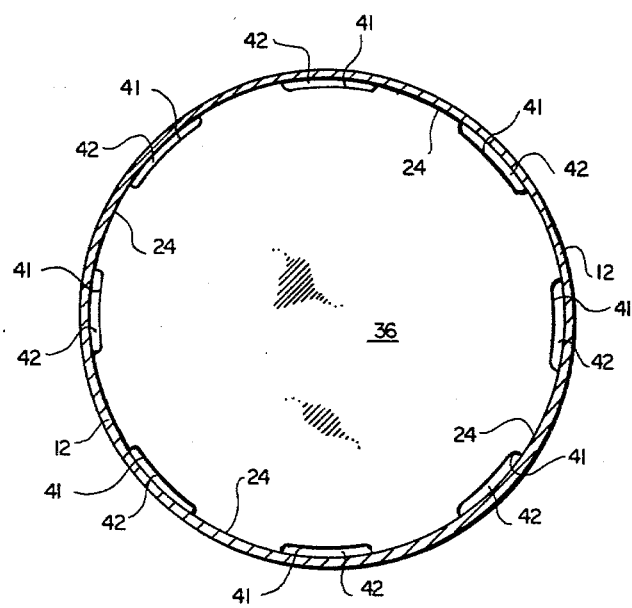
FIG. 5 is a top sectional view depicting the separating plate in position within the cavity of the container, this view being taken along line 5—5 of FIG. 1.

As is best illustrated in FIG. 5, plural apertures 42, radially spaced about the periphery of separating plate 36, are provided for fluid communication between first chamber 38 and second chamber 40. Apertures 42 permit the degassed biological fluids to pass from the first chamber to the second chamber, wherein they are collected for transmission from the bubble trap through exit port 18. From that Figure, it will be appreciated that apertures 42 preferably comprise a plurality of notches radially spaced at equidistant intervals about the periphery of separating plate 36 which, when in position adjacent to inner wall 24, define elongated slot-shaped apertures for transmission of biological fluids. As shown in FIG. 4, the upper surface of separating plate 36 preferably has a convex shape with respect to first chamber 38. With the upper surface of the separating plate being so shaped the biological fluids are directed towards apertures 42. The lower surface of separating plate 36 is preferably convex with respect to second chamber 40, and thus separating plate 36 comprises a double convex baffle. While the lower surface of separating plate 36 is depicted as being convex with respect to second chamber 40, it will be appreciated that this lower surface may have another convenient shape.

Separating plate 36 is removably connected to inner wall 24 by attachment of its peripheral edge to side wall 24, with the upper peripheral edge of the separating plate 36 abutting shoulder 44 which is formed in side wall 24. Plate 36 may be connected by commonly known adhesive means, or alternatively, by comformably threading the outer peripheral edge of plate 36 into the corresponding surface adjacent to and below shoulder 44. The removability of plate 36 provides for access to the interior of bubble trap 10.

The Method

As previously indicated, the present device may be utilized in transfusion or bypass systems for removing gas bubbles which have inadvertently appeared within the transferred biological fluids. The method of removing gas bubbles is best understood by reference to FIGS. 1-4.

The incoming biological fluids are injected into container 12 through inlet port 14, which is connected to a transfusing or bypassing system (not shown) by connector 20. The injected biological fluids flow through inlet port 14 tangentially onto the surface of container wall 24 (see FIG. 3) with sufficient velocity to create a vortex action as the fluids are forced in a circular motion within container 12 around the interior surface of side wall 24.

The centrifugal force created by the vortex movement of the biological fluids causes an increase in the fluid to gas density ratio. Because of the buoyancy of the gas bubbles in the fluid as it is being circulated around the interior of the bubble trap, the gas bubbles tend to move toward the center of first chamber 38 (see FIG. 4). In addition, there is the effect of gravity acting upon the gas bubbles in the circulating fluids which induces the gas bubbles to move toward the upper portion of first chamber 38. The resultant effect is that the gas bubbles "rise" from the fluid toward the upper and center portion of first chamber 38 where they are vented through vent port 16. Vent port 16 may be connected to a further external venting system (not shown). Vent port 16 may also be connected to a pressure monitoring device, in order to determine the pressure build-up inside the chamber, if any.

Since vent port 16 is positioned at the apex of ceiling surface 26 and since container wall 24 slopes generally outwardly from top to bottom, the effects of the gravitational pull upon fluid entering the bubble trap are enhanced with the result that the fluids are drawn downwardly with time, thereby preventing contact between those fluids and vent port 16.

An appreciation of the interrelationship of the gravitation and centrifugal forces which act upon the gas bubbles in the circulating biological fluids can be obtained from the following example. Blood was injected into a device within the scope of the present invention having an inside diameter of about three inches. A linear flow velocity of 1305 inches per minute at a flow rate of 6 liters per minute is typical of that used in cardiopulmonary bypass circuits. When the blood flows through inlet port 14 (with optimally minimal friction because the blood enters the bubble trap tangentially to side wall 24), the linear velocity of 1305 inches per minute is converted to a rotational velocity of 139 rpm. The relative centrifugal forces created by such a flow is 0.82 times the force of gravity. Hence, there is a centrifugal buoyancy of about 0.82 g which forces the gas bubbles towards the center of chamber 38.

In addition, there is the gravitation force of 1.0 g resulting from normal gravity which forces the gas bubbles toward the upper portion of chamber 38. Consequently, the separatory buoyancy of 1.0 g upwards vectorially added to the separatory buoyancy inwards yield a 1.29 g separatory influence on the gas bubbles in the blood from the bottom periphery of first chamber 38 to the top center portion of the first chamber.

It will be readily appreciated that by controlling the velocity at which the fluids are injected through inlet port 14, the amount of the centrifugal forces on the fluids and gas bubbles can be controlled. While it is desirable to maximize the centrifugal forces, care must be taken so as not to damage the fluids. In the situation where blood is being degassed, severe sheer forces or stresses can cause damage to the blood cells, such as hemolysis. However, it has been found that the linear velocity of fluids typically used in most medical procedures can be translated into a rotational velocity which does not damage the blood cells. Moreover, it is desirable to maintain a relatively constant fluid flow into the bubble trap and optimally to minimize any friction as the blood enters the bubble trap.

As the biological fluids progress downward within chamber 38 towards the upper surface of separating plate 36, the velocity of the fluids decreases. By the time such fluids reach the separating plate and apertures 42, the gas bubbles will have been removed and the degassed biological fluids will pass by gravitational action through apertures 42 into collecting chamber 40. The circulating speed of the fluids will have decreased by the time the fluids reach separating plate 36 such that there will be little shear force on the fluid as it comes into contact with apertures 42.

The floor surface 29 of chamber 40 is sloped downwardly and inwardly toward its lowermost center point such that the degassed biological fluid is drawn by gravitational forces toward exit port 18. The degassed fluids then pass through exit port 18 to other portions of the transfusion or bypass system, such as to an infusion point, by interconnection of the system with attached connector 20.

Thus, according to the present invention biological fluids may be rapidly degassed and collected for infusion or other processes without suffering the effects of hemolysis, within a container of limited space requirements. Moreover, large quantities of fluids need not be collected before the degassing process can be accomplished.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for separating gas bubbles from blood comprising:
means for injecting blood generally tangentially onto the interior surface of a cavity so as to create a vortical flow of the blood with minimal hemolysis of said blood, thereby utilizing centrifugal forces caused by said vortical flow to separate the gas bubbles from the blood to produce essentially degassed blood;
a double convex baffle having a convex upper surface and a convex lower surface and being positioned within the cavity so as to form a first chamber and a second chamber in the cavity, said baffle being configured to minimize shear forces acting on the blood said baffle further having at least one opening providing communication between the first and second chambers such that the degassed blood may be collected in the second chamber;
means for removing said separated gas bubbles from said cavity; and
means for transmitting the degassed blood from said cavity.

2. An apparatus as defined in claim 1 wherein said cavity forms an interior surface which is generally cylindrical and said convex baffle extends between and generally perpendicular to said interior surface of the cavity.

3. An apparatus for separating gas bubbles from blood comprising:
a housing defining a cavity therein, said cavity having a generally cylindrical interior surface;
a first port in said housing being generally tangentially oriented with respect to the interior surface of the cavity, through which the blood may be introduced into said cavity with a minimal amount of hemolysis so as to create a vortical flow of the blood such that centrifugal forces caused by said vortical flow and gravitational forces separate the gas bubbles from the blood to produce essentially degassed blood;
a generally circular double convex baffle having and being a convex upper surface and a convex lower surface positioned between and generally perpendicular to said interior surface near a lower portion of said cavity thereby forming a first chamber and a second chamber within said cavity, said baffle being configured so as to minimize shear forces acting on the blood said baffle further having at least one opening providing communication between the first and second chambers such that the degassed blood may be collected in the second chamber;
a second port in said housing through which the separated gas bubbles may be removed from the cavity; and
a third port in said housing through which the degassed blood is transmitted out of said second chamber.

4. An apparatus as defined in claim 3 wherein the cross-sectional diameter of the cavity increases from the first port to the third port.

5. An apparatus as defined in claim 4 wherein said increased cross-sectional diameter produces an increased downward flow of the degassed blood toward the third port.

6. An apparatus as defined in claim 3 wherein the blood in said vortical flow is caused to move from the first port toward the third port by gravity.

7. An apparatus as defined in claim 6 wherein the gas bubbles are caused to move toward the second port by said centrifugal and gravitational forces acting upon the blood.

8. An apparatus as defined in claim 3 wherein the openings comprise apertures which are located around the peripheral edge of the baffle.

9. An apparatus for separating gas bubbles from blood comprising:
a container having an interior surface of a truncated conical shape such that its top end intersects with a concave top portion and its bottom end intersects with a concave floor section;
a double convex baffle extending between and generally perpendicular to the interior surface of the container forming first and second chambers within the container, said baffle being configured so as to minimize shear forces acting on the blood;
a plurality of apertures adjacent the peripheral edge of said baffle, said apertures providing for fluid communication between said first and second chambers;
a first port extending from the exterior of the container into the first chamber, said first port being oriented such that blood may be injected through the first port and introduced tangentially onto the interior surface of the first chamber with a minimal amount of hemolysis to said blood and so as to create a vortical flow;

a second port extending from the apex of said concave top portion to the exterior of said container providing for venting of gas bubbles separated from the blood; and a third port extending from the lowermost portion of the floor of said second chamber to the exterior of said container providing for removal of the blood after the gas bubbles have been separated therefrom.

10. A method for separating gas bubbles from blood, the method comprising the steps of:

introducing blood into a first chamber in a cavity in such a manner that hemolysis of the blood is minimized and such that said blood has a vortical flow;

separating gas bubbles from the blood to produce essentially degassed blood by utilizing centrifugal forces which are caused by said vortical flow;

venting the gas from the cavity;

directing the blood downward along the interior walls of the first chamber and outward along the upper curved surface of a double convex baffle having a convex upper surface and a convex lower surface so as to collect said blood adjacent said interior walls and adjacent an outer perimeter of said baffle;

passing the blood through apertures adjacent the perimeter of the double convex baffle and into a second chamber in the cavity; and transmitting the degassed blood from the cavity.

11. A method as defined in claim 10 further comprising the step of collecting the degassed blood in a lower portion of the cavity prior to transmission of such degassed biological fluids from the cavity.

12. A method as defined in claim 11 further comprising the step of directing gas upward and outward along the lower curved surface of the convex baffle so as to transfer said gas upward through the apertures in the first chamber as said gas is displaced by blood within the second chamber.

13. A method as defined in claim 10 wherein the vortical flow of the blood is gradually directed in a downward direction due to gravity.

14. A method as defined in claim 13 wherein said gravitational forces aid in the separating of the gas bubbles from the blood.

15. A method for separating gas bubbles from blood, the method comprising the steps of:

introducing blood into a first chamber in a container so as to minimize hemolysis of said blood and such that said blood has a vortical flow;

separating gas bubbles from the blood by utilizing centrifugal forces which are caused by said vortical flow and by utilizing gravitational forces;

removing the separated gas bubbles from the first chamber through an aperture extending from the first chamber to the exterior of said container;

directing the blood downward along interior walls of the first chamber and outward along the upper curved surface of a double convex baffle so as to collect said blood adjacent said interior walls and adjacent an outer perimeter of said baffle;

transferring the blood from which the gas bubbles have been separated through apertures adjacent the perimeter of the double convex baffle into a second chamber through utilization of gravity;

collecting the blood in said second chamber; and removing said collected blood from the second chamber through an aperture extending from the second chamber to the exterior of the container.

* * * * *

UNITED STATES PATENT AND TRADEMARK OFFICE
CERTIFICATE OF CORRECTION

PATENT NO. : 4,345,919
DATED : August 24, 1982
INVENTOR(S) : WILLIAM R. WILKINSON et al.

It is certified that error appears in the above—identified patent and that said Letters Patent is hereby corrected as shown below:

Column 4, line 67, "sheer" should be --shear--

Column 7, line 31, "biological fluids" should be --blood--

Column 8, line 1, "in" should be --into--

Signed and Sealed this

Ninth Day of November 1982

[SEAL]

Attest:

Attesting Officer

GERALD J. MOSSINGHOFF

Commissioner of Patents and Trademarks